United States Patent [19]

Balsam et al.

[11] Patent Number: 5,155,546
[45] Date of Patent: Oct. 13, 1992

[54] METHOD FOR QUANTITATIVE DETECTION OF ORGANIC MATERIALS IN ROCKS AND SEDIMENTS USING VISIBLE LIGHT SPECTRA

[75] Inventors: William L. Balsam, Arlington; Bobby C. Deaton, Forth Worth, both of Tex.

[73] Assignee: Texas Wesleyan University, Inc., Fort Worth, Tex.

[21] Appl. No.: 709,598

[22] Filed: Jun. 3, 1991

[51] Int. Cl.$^5$ .............................................. G01J 3/00
[52] U.S. Cl. ..................................... 356/300; 356/319
[58] Field of Search ........................... 356/445–448, 356/70, 72, 241, 300, 319

[56] References Cited

U.S. PATENT DOCUMENTS

| | | | |
|---|---|---|---|
| 2,334,475 | 11/1943 | Clavdet | 250/71 |
| 3,787,695 | 1/1974 | West | 250/365 |
| 3,961,187 | 6/1976 | Barringer | 250/301 |
| 4,009,962 | 3/1977 | Laver et al. | 356/70 |
| 4,149,804 | 4/1979 | Chew, III | 356/448 |

OTHER PUBLICATIONS

Holden et al, "The Observation of Spectral Variation Indicative of Prophyrin Biomarkers in Reflectance Spectra of Source Rock: The Application of Remote Sensing Technology to Petroleum Geochemistry", Seventh Thematic Conference on Remote Sensing for Exploration Geology, Oct. 2–6, 1989.

Primary Examiner—F. L. Evans
Assistant Examiner—K. P. Hantis
Attorney, Agent, or Firm—Geoffrey A. Mantooth

[57] ABSTRACT

A method for quantitatively determining the total organic carbon and vitrinite reflectance of rocks and sediments utilizes the entire visible light spectrum. A sample is prepared and placed in a spectrophotometer. The spectrophotometer has a light source that produces the entire visible light spectrum. A monochromator passes narrow wavelength bands of the source light therethrough to illuminate the sample. The total diffuse reflectance spectrum is obtained from the sample using the spectrophotometer. The reflectance spectral data are processed by determining the first derivative and by comparing it to calibration data of known total organic carbon and vitrinite reflectance.

8 Claims, 4 Drawing Sheets

METHOD FOR QUANTITATIVE DETECTION OF ORGANIC MATERIALS IN ROCKS AND SEDIMENTS USING VISIBLE LIGHT SPECTRA

FIELD OF THE INVENTION

The present invention relates to methods for detecting organic materials in rocks and sediments and for estimating the thermal maturity of rocks and sediments.

BACKGROUND OF THE INVENTION

In the search for oil and gas deposits, seismic surveys are typically performed in order to locate likely prospects (or areas) having oil and gas. If an area looks promising, then a well may be drilled so as to penetrate down to the reservoir. When drilling the well, samples of the rocks and sediments brought up from the borehole are tested directly to identify oil or gas bearing zones. As the drill bit penetrates through a zone of interest, samples of the rock or sediment are brought to the surface for testing.

In particular, two parameters, total organic carbon content (or TOC) and vitrinite reflectance, are used in the petroleum industry as diagnostic tools for determining potential oil or gas bearing zones. If the rock samples contain a sufficient amount of TOC and are in the appropriate range of vitrinite reflectance values, then there is a strong potential that oil or gas have been produced in the zone of interest. TOC indicates the quantitative amount of organic material present in the sample. Samples with a sufficient amount of organic carbon are candidates as sources for oil or gas. Vitrinite is an organic material made up of plant debris. Vitrinite reflectance indicates the thermal maturity of the sample. Oil and gas are generated in a narrow range of thermal maturities which is estimated by the vitrinite reflectance of a sample.

Prior art methods for testing for TOC are imprecise, slow, expensive or are unable to quantify the amount of TOC. One prior art method which is fast but imprecise involves a geologist or other trained person visually examining and smelling the sample. The more organic material that is present, the darker the sample will appear. Another prior art method of testing for TOC involves substantial chemical analysis. The amount of all of the carbon in the sample is determined by combusting a portion of the sample in an oxygen stream. The total carbon includes inorganic or mineral carbon, as well as organic carbon. The amount of mineral carbon is determined by acid digestion of another portion of the sample. To determine the amount of organic carbon, the amount of mineral carbon is subtracted from the amount of total carbon. This method is slow and destroys the sample.

A prior art method that tests for vitrinite reflectance is undesirable because it is inherently subjective and imprecise. It involves grinding and digesting a sample in acid to concentrate organic material. The remains are then examined with a microscope that has been equipped with an oil immersion lens. A human operator visually identifies those pieces that are vitrinite and estimates their reflectance.

SUMMARY OF THE INVENTION

It is an object of the present invention to provide a method for detecting organic materials in rocks and sediments in a rapid and quantitative manner.

It is a further object of the present invention to provide a method for quantifying the amount of total organic carbon material and for determining the vitrinite reflectance and thermal maturity of a rock or sediment sample.

The method of the present invention detects organic materials in a sample. Means for obtaining a total reflectance spectrum from this sample are provided. The sample is placed in the means for obtaining a total reflectance spectrum. Then, the sample is illuminated in the means for obtaining a total reflectance spectrum with an electromagnetic spectrum that comprises the entire visible light spectrum. A total reflectance spectrum is obtained from the sample. The sample total reflectance spectrum is related to a reference reflectance spectrum to determine the total organic carbon content of the sample and the vitrinite reflectance of the sample. The reference reflectance spectrum has a known total organic carbon content and a known vitrinite reflectance.

With the method of the present invention, the total organic carbon and vitrinite reflectance can be quantitatively determined by using the entire visible light spectrum to produce a total diffuse reflectance spectrum from the sample. Use of the entire visible light spectrum to obtain a total reflectance spectrum from the sample provides informative data on the total organic carbon and vitrinite reflectance of the sample. This informative data enables a more precise measurement of the oil or gas bearing properties of the sample. Prior art methods can make only qualitative determinations, wherein the mere presence of organic carbon and vitrinite reflectance is detected.

In addition, the method of the present invention enables rapid testing of a sample for total organic carbon and vitrinite reflectance. In just a few minutes, the sample can be tested and the amount of total organic carbon and the vitrinite reflectance value determined. The sample can be tested at the drilling site to provide an almost real time assessment of the progress of the drilling operations. Furthermore, the equipment used, a spectrophotometer and a personal computer, are each relatively inexpensive.

In one aspect, the first derivative of the total diffuse reflectance spectrum is determined to better interpret the data. This is particularly useful where the reflectance spectrum appears to be smooth and featureless. Rock and sediment samples from boreholes that contain organic material are typically dark, indicating that the samples exhibit low reflectance. For some samples, the reflectance may be as low as 8% or less. These dark samples provide reflectance spectra that are close to the detection threshold of the spectrophotometer. By determining the first derivative of the reflectance spectrum, the interesting portions of the reflectance spectrum become evident, even at a low reflectance. This enables a more accurate comparison with reference spectra.

BRIEF DESCRIPTION OF THE DRAWINGS

FIG. is a side cross-sectional view of the equipment used to practice the method of the present invention, in accordance with a preferred embodiment.

DESCRIPTION OF PREFERRED EMBODIMENT

The method of the present invention determines quantitatively the amount of total organic carbon (TOC) in a rock or sediment sample. The sample is illuminated with the entire visible light spectrum to produce a reflectance spectrum. This reflectance spectrum is then analyzed to determine the TOC. In addition, the method utilizes the reflectance spectrum to determine the vitrinite reflectance (Ro) of the sample. TOC and vitrinite reflectance are measures that are used by the petroleum industry to indicate the presence of oil or gas in the sample and thus in the zone that produced the sample. TOC indicates the amount of organic material present in the sample. Vitrinite reflectance indicates the thermal maturity of the sample. A sufficient amount of thermal maturity is considered necessary for a formation to contain oil or gas.

Figure 1:
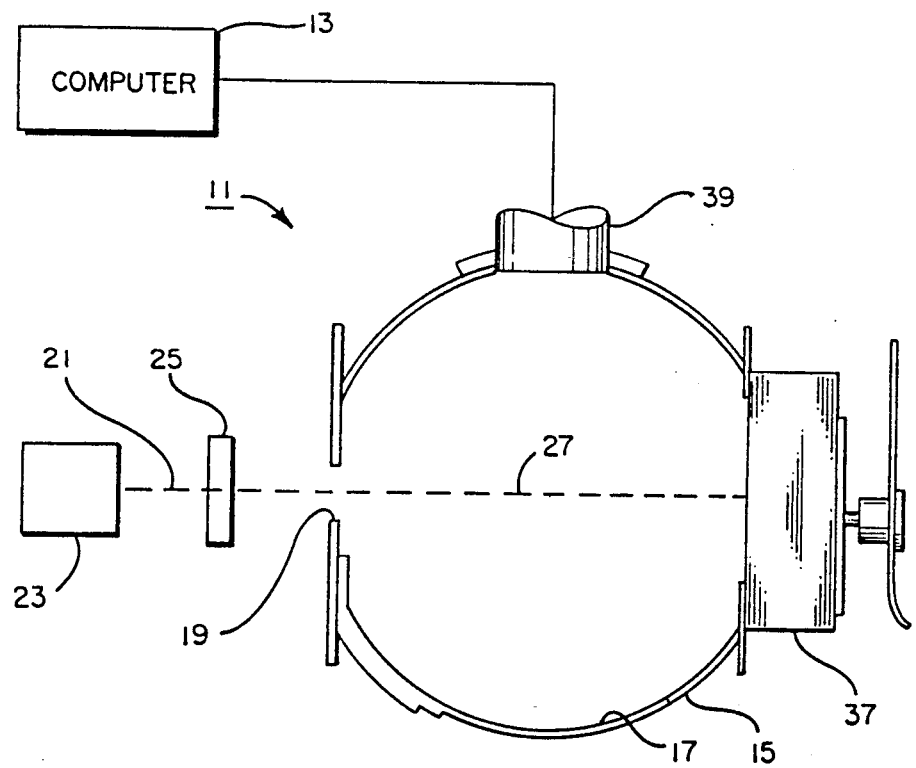
Figure 2:
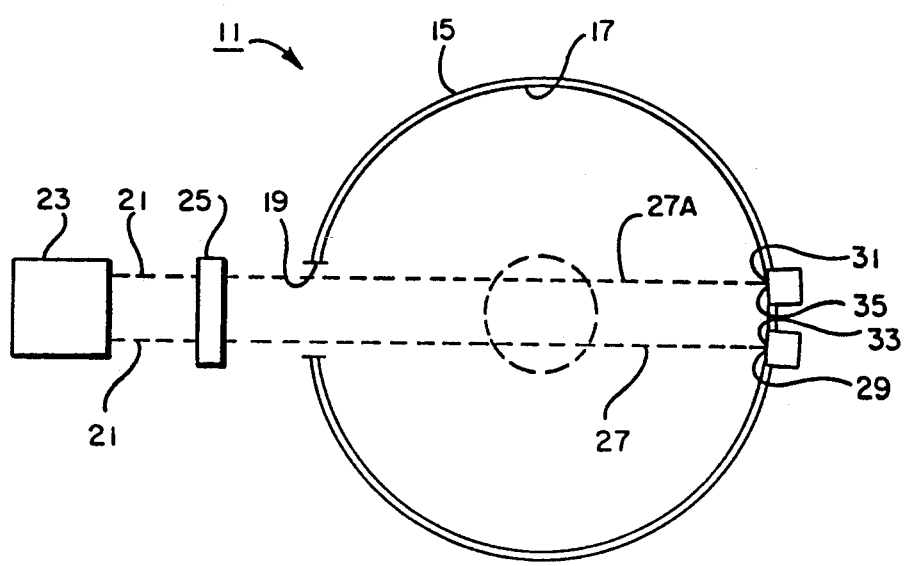
FIG. 2 is a top cross-sectional view of the total reflectance sphere in the spectrophotometer of FIG. 1, showing the reference and the sample being tested.

In FIGS. 1 and 2, there are shown views of the equipment used for practicing the method of the present invention, in accordance with a preferred embodiment. The equipment includes a spectrophotometer 11 fitted with a total reflectance apparatus and a computer 13.

The spectrophotometer 11 is a conventional commercially available device. The spectrophotometer 11 is fitted with a diffuse reflectance sphere 15 which allows the measurement of diffused light reflected from a target object. This sphere 15 has a hollow interior; the interior surface of this sphere is coated with a white reflective material 17 to obtain the total, diffuse reflectance from a sample. The sphere 15 has an inlet port 19 for allowing light to pass from the outside of the sphere to the interior. A light source 23 is provided to shine light 21 into the sphere by way of the inlet port 19. The light source 23 provides white light 21, wherein the entire visible light spectrum is produced. Visible light is electromagnetic radiation having a wavelength in the range of about 390 nanometers (nm) to about 770 nanometers. Alternatively, another commonly accepted definition of visible light is electromagnetic radiation having a wavelength in the range of 400 to 700 nanometers. The light 21 produced by the source 23 is broken into two beams prior to entering the reflectance sphere 15. A monochromator 25 is interposed between the light source 23 and the inlet port 19. The monochromator 25, which in the preferred embodiment is a diffraction or holographic grating, passes narrow bands 27, 27A of the visible light spectrum produced by the source 23. The grating 25 is movable so as to control the particular band of light that is passed therethrough.

The sphere 15 has two object ports 29, 31 located across from corresponding inlet ports. The object ports are located side-by-side. One port is a sample port 29 while the other is a reference port 31. Respective glass microslides 33, 35 are used to carry the sample and the reference material. Holding apparatuses 37 are provided to hold the microslides in position adjacent to ports.

A receiver 39 is provided at the top portion of the sphere. The receiver 39 is a photomultiplier tube or other detector that measures the intensity of the reflected light from the sample surface. The receiver is sensitive to the entire visible spectrum. The receiver converts the light collected from the sphere into an electrical signal, which is passed on to the computer.

The computer 13 is a conventional, commercially available device which displays and stores the data from spectrophotometer 11. The computer 13 also performs data processing as will be explained in more detail hereinafter.

The method of the present invention will now be described. First, the sample material which is to be tested is prepared for the reflectance measurement. The sample rock or sediment is ground up in a mortar and pestle. The mortar and pestle are made of a very hard material such as diamite in order to adequately grind any hard minerals contained in the sample. The sample is ground to a fine powder, having a particle size of about 30 microns or less. Then, four to five drops of distilled water or alcohol are deposited on a clean glass microslide. About 0.15 grams of the powdered sample material is added to the liquid so as to form a slurry. This slurry is spread and smoothed out on the microslide 33. The thickness of the slurry should be sufficient so that light will not penetrate therethrough. However, the slurry should not be so thick as to crack when dry. It is estimated that the slurry is about 40–50 microns thick. The slurry is allowed to dry at room temperature. Alternatively, the drying process can be speeded up by placing the microslide on a hot plate set to about 40–50 degrees Celsius. Alternatively, instead of using ground samples mounted on slides, powders or polished fragments of rock may be placed directly in the spectrophotometer sample port 29.

Before the sample microslide is placed into the spectrophotometer 11, the spectrophotometer is initialized. Reference material mounted on microslides are located in each of the sample and the reference ports 29, 31. Various reference materials are available including barium sulfate, magnesium oxide, aluminum oxide and several polymers. The reference material has a 100% reflectance of all of the wavelengths in the visible light spectrum. The source light 21 is turned on and the monochromator 25 steps through the visible light spectrum, as will be explained hereinafter.

After the spectrophotometer has been initialized, the sample microslide 33 or polished sample is placed into the sample port 29 of the spectrophotometer 11. The reference material in the reference port 31 is kept in place.

With the sample and reference microslides 33, 35 in place in the spectrophotometer 11, the source 23 is turned on. The reference and the sample are scanned by the various wavelengths of the source light. The diffraction or holographic grating 25 breaks or monochromates the source light into specified wavelength intervals. In the preferred embodiment, the wavelength intervals used are one nanometer. Beginning at one end of the spectrum, the monochromated beam 27 at the specified wavelength interval is first shown on the sample. The beam 27 is focused so as to shine only on the sample and not on the reference. The sample reflects a portion of the monochromated source light back into the sphere. The total diffused reflected light from the sample is collected by the receiver 39. Then, the monochromated beam 27A is shown on the reference. The focused beam shines only on the reference and not on the sample. The total diffused reflected light from the reference is collected by the receiver 39. The source light is manipulated between the sample and the reference by the grating.

After both the sample and the reflectance materials have been exposed to the monochromated source light, the grating is moved to the next specified wavelength increment and the illumination procedure is repeated. The sample and reference are ultimately exposed to the entire visible spectrum of light.

The spectrophotometer 11 measures reflectance intensity as a function of wavelength. Thus, in the preferred embodiment, the reflectance intensity is measured for every specified wavelength interval over the visible light spectrum. The reflectance intensity for each wavelength interval is the ratio of the amount of light reflected from the sample divided by the amount of light incident on it. The amount of light reflected from the sample is measured when the source light is shown on the sample. The amount of light incident on the sample is measured when the source light is shown on the reference, which has 100% reflectance. The reflectance intensity is expressed as a percentage.

These raw reflectance intensity data are stored on a medium (floppy disk, hard disk, optical disk, tape, etc.) readable by the computer 13.

Figure 3:
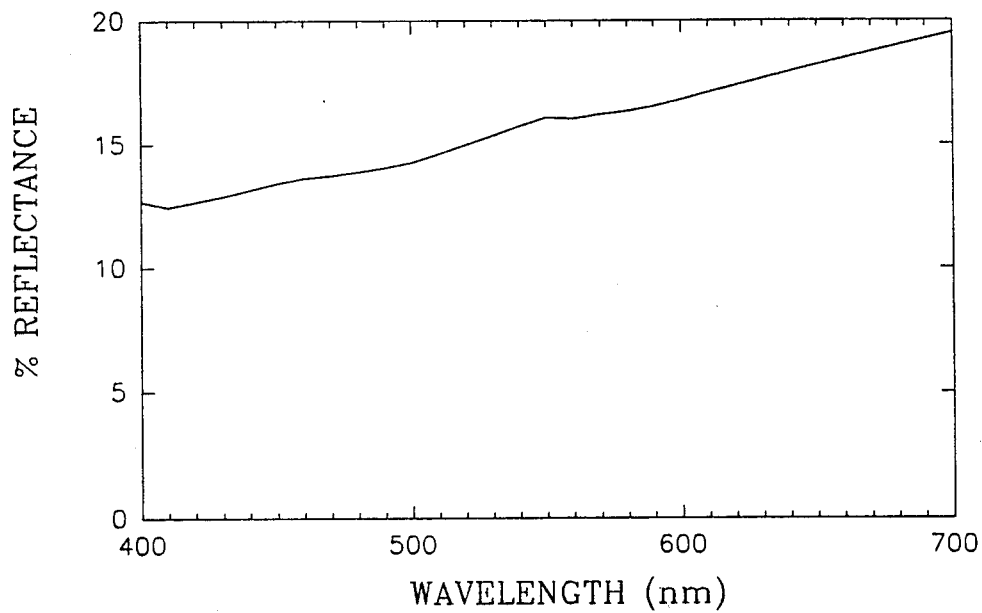
FIG. 3 is a graph showing a typical raw spectral curve from a sample, obtained with the method of the present invention.
Figure 4:
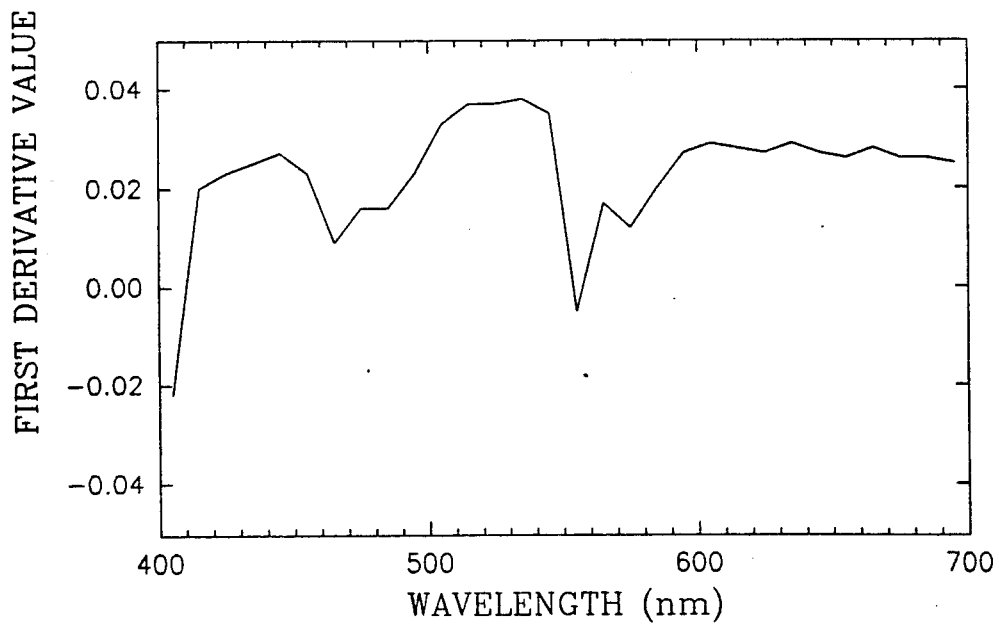
FIG. 4 is a graph showing the first derivative curve, obtained from the raw spectral curve of FIG. 3.

The raw reflectance intensity data from the sample (hereinafter referred to as sample data) are then processed by the computer 13 to extract information regarding the total organic carbon content in the sample and the vitrinite reflectance of the sample. The sample data are typically smooth and featureless (see FIG. 3). In order to better interpret the data, the first derivative of the reflectance intensity, with respect to wavelength, is determined (see FIG. 4). The first derivative data exhibit peaks at those wavelengths that are at the edges of the absorption bands of the particular sample being tested.

The next step is to identify those portions, if any, of the sample data that are produced by organic carbon material and vitrinite. In order to identify the organic carbon and vitrinite portions of the sample data, the sample data are compared to an organic carbon and a vitrinite reflectance calibration or reference data set.

The calibration data set consists of plural reflectance spectra taken from samples for which both the total organic carbon content (TOC) and vitrinite reflectance (Ro) have been determined by established prior art techniques. Thus, the calibration data set reflectance spectra have known amounts of TOC and Ro. The first derivative, with respect to wavelength, of the spectra in the calibration data set is determined.

In the preferred embodiment, the TOC and Ro portions of the sample data are determined by using multiple linear regression. Using the calibration data and comparing it to the sample data, multiple linear regression determines a respective polynomial, or mathematical model, for TOC and Ro of the sample data. Once the polynomial is determined, then TOC and Ro of the sample can be quantitatively determined.

The quantitative amounts of TOC and Ro in the sample are determined as follows. After the first derivative of the sample data is determined, the nature of the organic material in the sample data is determined. The organic material in the sample data is characterized as either kerogen-like or bitumen-like. Both kerogen and bitumen are derived from plant material. Kerogen-like organic material exhibits an absorption band at the violet end of the visible spectrum, while bitumen-like organic material exhibits an absorption band that extends across the visible spectrum into the orange region. The characterization as either kerogen-like or bitumen-like can be determined using established curve deconvolution techniques (such as Fourier analysis or factor analysis) or by using commerically available curve analysis software (for example, PeakFit from Jandel Scientific).

After characterizing the sample as either kerogen-like or bitumen-like, those reflectance specta in the calibration data set that are dominated by one of the types of organic material in the samples are selected. For example, if the sample is characterized as being kerogen-like, the kerogen-like reflectance spectra of the calibration data set are selected. The calibration data set contains reflectance spectra that are dominated by kerogen-like organic material and also reflectance spectra that are dominated by bitumen-like organic material.

Continuing with the example, the kerogen-like reflectance spectra are regressed to produce a predictive model for use on the sample reflectance spectra. A model is produced for TOC and another model is produced for Ro using the calibration data set. Based on our calibration data set to date, we have developed the following models:

1. TOC in kerogen
   $TOC = -196.220(X_{405}) + 183.139(X_{415}) + 362.112(X_{455}) + -376.199(X_{485}) + -547.015(X_{495}) + 895.879(X_{585}) + -382.399(X_{615}) + 687.677(X_{635}) + -875.217(X_{695})$
2. Ro in kerogen
   $Ro = 23.874(X_{405}) + -96.724(X_{445}) + 36.079(X_{465}) + 116.697(X_{515}) + 64.971(X_{545}) + -49.545(X_{555}) + -44.194(X_{585}) + -176.070(X_{625}) + 123.929(X_{685})$
3. TOC in bitumen
   $TOC = -76.126(X_{435}) + -127.804(X_{445}) + 81.193(X_{455}) + 282.132(X_{535}) + -534.575(X_{595}) + -385.834(X_{625}) + 755.760(X_{635}) + 506.000(X_{645}) + 148.239(X_{655}) + -383.606(X_{675}) + -328.106(X_{685})$
4. Ro in bitumen
   $Ro = -39.832(X_{445}) + -158.693(X_{455}) + -173.670(X_{465}) + -69.630(X_{555}) + -120.028(X_{565}) + -84.349(X_{575}) + 313.398(X_{605}) + -449.993(X_{635}) + 177.361(X_{655}) + -50.658(X_{695})$ Wherein TOC is total organic carbon content, Ro is vitrinite reflectance and $X_{xxx}$ is the first derivative value at the wavelength $xxx$ in nanometers.

These models utilize the first derivative values at certain frequencies of interest. The constants are weighting factors that allow some wavelength values to be weighted more or less heavily than other wavelength values.

These models make up a reference against which the sample data are compared. The amount of TOC and Ro are quantitatively determined by using the first derivative values of the sample data in the appropriate model. For example, if the sample data has been characterized as kerogen-like, then TOC is determined using equation (1) and Ro is determined using equation (2).

Figure 5:
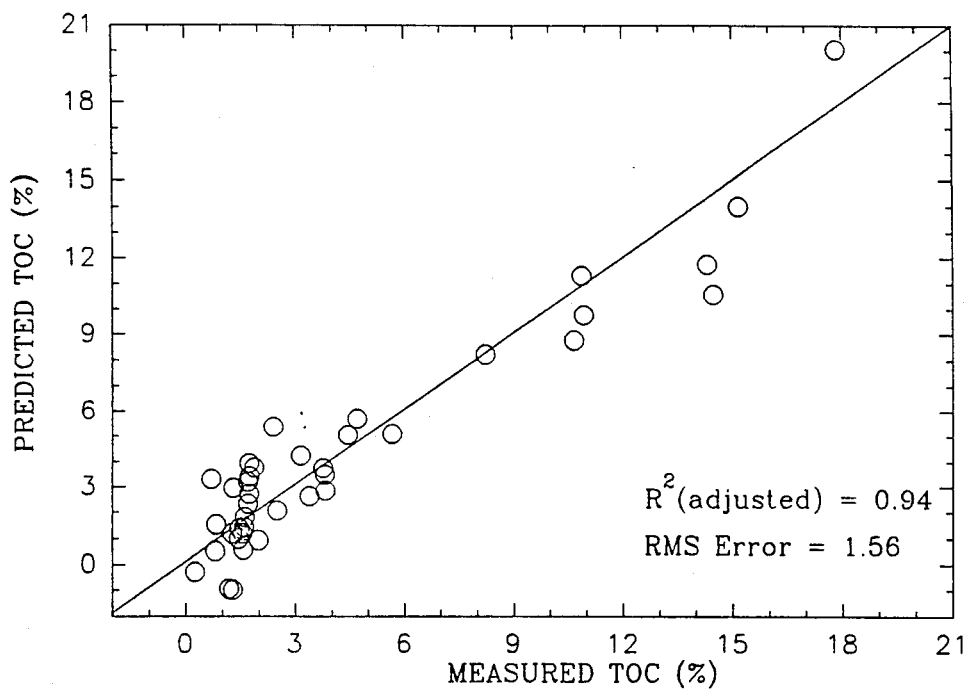
FIG. 5 is a graph showing the correlation between predicted total organic carbon and measured total organic carbon for kerogen-like organic matter.
Figure 6:
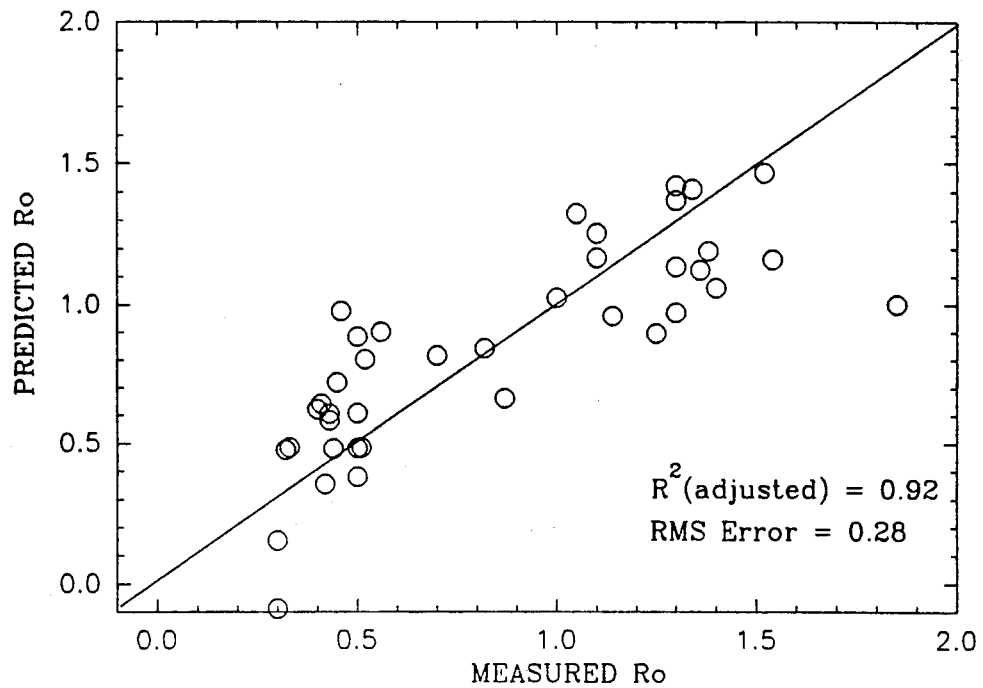
FIG. 6 is a graph showing the correlation between predicted vitrinite reflectance and measured vitrinite reflectance for kerogen-like organic matter.
Figure 7:
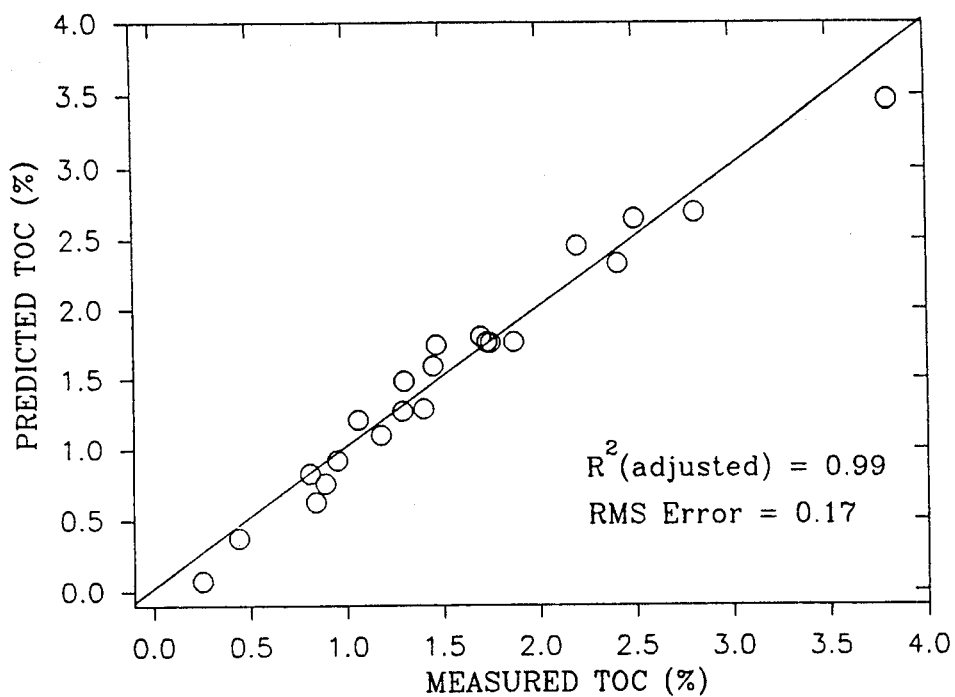
FIG. 7 is a graph showing the correlation between predicted total organic carbon and measured total organic carbon for bitumen-like organic matter.
Figure 8:
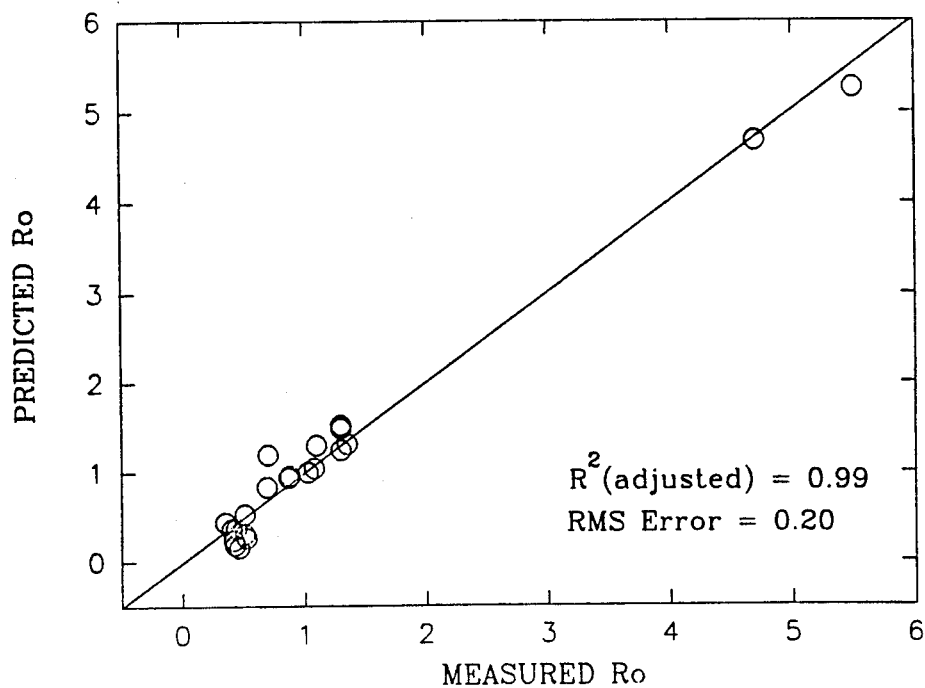
FIG. 8 is a graph showing the correlation between predicted vitrinite reflectance and measured vitrinite reflectance for bitumen-like organic matter.

We have found that by using the method of the present invention, the amount of TOC and Ro can be determined with surprising accuracy. One way to determine the accuracy of the method is by determining correlation coefficients, wherein the accuracy of the models is determined. A correlation coefficient of 1 is perfect or ideal. All of the equations had a correlation coefficient in excess of 0.92. Another way to determine the accuracy of the method is to graphically plot the measured value of either TOC or Ro for a sample as a function of the predicted value of TOC or Ro. FIG. 5 shows the correlation between predicted TOC and measured TOC for kerogen-like organic matter. If the correlation was ideal, then these values would lie on a straight line. FIG. 6 shows the correlation between predicted Ro and measured Ro for kerogen-like organic matter. FIGS. 7 and 8 show the respective correlations between predicted TOC and measured TOC and predicted Ro and measured Ro for bitumen-like organic matter. As these graphs show, the accuracy of the method of the preferred embodiment is quite good.

Ideally, the reflectance spectra in the calibration data set will encompass the full range of visible light reflectance, TOC and Ro variations present in the samples being tested. Our calibration data set currently uses a relatively small number (about 70) of reflectance spectra. As data are added to the calibration data set, the range of variation inevitably will increase. Therefore, the models given above will likely change to reflect the increased accuracy of the expanded calibration data set. Likewise, a variety of quantitative methods, other than the multiple linear regression technique described above, may be used to determine TOC and Ro. For example, other types of regression, such as geometric, exponential or harmonic, could be used. In lieu of factor analysis, Fourier series analysis of the reflectance spectra and harmonic regression could be performed to quantitatively determine the amount of TOC and Ro in the sample.

Furthermore, as the calibration data set expands, the sample data may be characterized more narrowly than kerogen-like or bitumen-like. Sample data, for example, could be characterized as a specific type of kerogen.

The foregoing disclosure and the showings made in the drawings are merely illustrative of the principles of this invention and are not to be interpreted in a limited sense.

We claim:

1. A method for detecting organic material in a sample, comprising the steps of:
    a) providing means for obtaining a total reflectance spectrum from said sample;
    b) placing said sample in said means for obtaining a total reflectance from said sample;
    c) illuminating said sample in said means for obtaining total reflectance with an electromagnetic spectrum comprising the entire visible light spectrum;
    d) obtaining a total reflectance spectrum from said sample;
    e) relating said total reflectance spectrum to a calibration reflectance spectrum to determine total organic carbon content of said sample and vitrinite reflectance of said sample. said reference reflectance spectrum having a known total organic carbon content and a known vitrinite reflectance.

2. The method of claim 1 further comprising the step of determining the edges of absorption bands of said sample from said total reflectance spectrum and using these edges to relate said total reflectance spectrum to said calibration reflectance spectrum.

3. The method of claim 1 further comprising the step of preparing said sample by powdering said sample.

4. A method of detecting total organic carbon content and vitrinite reflectance of a sample rock, sediment, or soil, said total organic carbon content and vitrinite reflectance being used to determine if said sample has oil or gas potential, comprising the steps of:
    a) providing means for obtaining a total diffuse reflectance spectrum from said sample
    b) placing said sample in said means for obtaining a total reflectance from said sample;
    c) illuminating said sample in said means for obtaining total reflectance with an electromagnetic spectrum comprising the entire visible light spectrum;
    d) obtaining a total diffuse reflectance spectrum from said sample;
    e) determining the first derivative of said total diffuse reflectance spectrum with respect to wavelengths of said illuminating visible light spectrum;
    f) determining the amount of total organic carbon and vitrinite reflectance of said sample by comparing said total diffuse reflectance spectrum to a calibration reflectance spectrum having a known total organic carbon content and vitrinite reflectance.

5. The method of claim 4 further comprising the step of preparing said sample by powdering said sample.

6. A method of detecting total organic carbon content and vitrinite reflectance of a sample rock, sediment, or soil, said total organic carbon content and vitrinite reflectance being used to determine if said sample has oil or gas potential, comprising the steps of:
    a) illuminating said sample with the entire visible light spectrum;
    b) obtaining the total diffuse reflectance spectrum for the entire visible light spectrum from said illuminated sample;
    c) comparing said reflectance spectrum to calibration reflectance spectra having known values of total organic carbon content and vitrinite reflectance and determining the amount of total organic carbon and vitrinite reflectance from said comparison.

7. The method of claim 6 further comprising the step of determining the edges of absorption bands of said sample from said total reflectance spectrum and using these edges to relate said total reflectance spectrum to said calibration reflectance spectra.

8. The method of claim 6 further comprising the step of preparing said sample by powdering said sample.

* * * * *